United States Patent
Pigamo et al.

(10) Patent No.: US 9,834,499 B2
(45) Date of Patent: *Dec. 5, 2017

(54) E-1-CHLORO-3,3,3-TRIFLUOROPROPENE PRODUCTION PROCESS FROM 1,1,3,3-TETRACHLOROPROPENE

(71) Applicant: ARKEMA FRANCE, Colombes (FR)

(72) Inventors: Anne Pigamo, Franceville (FR); John Wismer, Washington Crossing, PA (US); Bertrand Collier, Saint-Genis-Leval (FR); Philippe Bonnet, Lyons (FR)

(73) Assignee: ARKEMA FRANCE, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/987,347

(22) Filed: Jan. 4, 2016

(65) Prior Publication Data

US 2016/0115104 A1  Apr. 28, 2016

Related U.S. Application Data

(63) Continuation of application No. 14/153,500, filed on Jan. 13, 2014, now Pat. No. 9,255,045.

(51) Int. Cl.
*C07C 17/20* (2006.01)
*C07C 17/25* (2006.01)
(Continued)

(52) U.S. Cl.
CPC ............ *C07C 17/206* (2013.01); *C07C 17/25* (2013.01); *C07C 17/38* (2013.01); *C07C 17/383* (2013.01); *C07B 2200/09* (2013.01)

(58) Field of Classification Search
CPC ....... C07C 17/25; C07C 17/20; C07C 17/206; C07C 17/38; C07C 17/383; C07C 17/07; C07C 17/04; C07C 17/06
See application file for complete search history.

(56) References Cited

U.S. PATENT DOCUMENTS 5,616,819 A   4/1997 Boyce et al.
5,684,219 A   11/1997 Boyce
(Continued)

FOREIGN PATENT DOCUMENTS

EP   0 940 382 A1   9/1999
FR   2768727 A1     3/1999
(Continued)

OTHER PUBLICATIONS

International Search Report issued in PCT/FR2015/050072, dated Apr. 16, 2015, 7 pages. European Patent Office, Rijswijk, NL.
(Continued)

*Primary Examiner* — Medhanit Bahta
(74) *Attorney, Agent, or Firm* — Buchanan Ingersoll & Rooney P.C.

(57) ABSTRACT

A production process for the production of E-1-chloro-3,3,3-trifluoropropene, the process including at least one stage during which 1,3,3,3-tetrachloropropene reacts with anhydrous hydrofluoric acid in the liquid phase, in the absence of a catalyst, with an HF/1,1,3,3-tetrachloropropene molar ratio between 3 and 20 inclusive, at a temperature between 50° C. and 150° C. inclusive and an absolute pressure of between 1 and 20 bar inclusive.

12 Claims, 1 Drawing Sheet

(51) Int. Cl.
*C07C 17/38* (2006.01)
*C07C 17/383* (2006.01)

(56) References Cited

U.S. PATENT DOCUMENTS

| | | |
|---|---|---|
| 5,877,359 A | 3/1999 | Elsheikh |
| 6,166,274 A | 12/2000 | Chen et al. |
| 8,346,217 B2 | 1/2013 | Crawford et al. |
| 8,404,907 B2 | 3/2013 | Nair et al. |
| 8,426,656 B2 | 4/2013 | Merkel et al. |
| 8,436,217 B2 | 5/2013 | Wang et al. |
| 9,255,045 B2 * | 2/2016 | Pigamo ............ C07C 17/206 |
| 2010/0191025 A1 | 7/2010 | Perdrieux |
| 2011/0197602 A1 | 8/2011 | Abbas et al. |
| 2011/0201853 A1 | 8/2011 | Tung et al. |
| 2011/0245549 A1 | 10/2011 | Merkel et al. |
| 2012/0059199 A1 | 3/2012 | Pokrovski et al. |
| 2012/0271070 A1 | 10/2012 | Wang et al. |
| 2012/0329893 A1 | 12/2012 | Abbas |
| 2013/0037058 A1 | 2/2013 | Abbas |
| 2013/0211154 A1 | 8/2013 | Cottrell et al. |
| 2013/0261354 A1 | 10/2013 | Merkel |
| 2015/0152235 A1 | 6/2015 | Abbas |
| 2015/0197467 A1 | 7/2015 | Pigamo et al. |
| 2016/0023974 A1 | 1/2016 | Bonnet et al. |

FOREIGN PATENT DOCUMENTS

| | | |
|---|---|---|
| WO | WO 2010/059496 A1 | 5/2010 |
| WO | WO 2010/111067 A1 | 9/2010 |

OTHER PUBLICATIONS

Rapport de Recherche Préliminaire, issued in FR1450381, Sep. 15, 2014, 3 pages, Institut National de la Propriété Industrielle, FR.

* cited by examiner

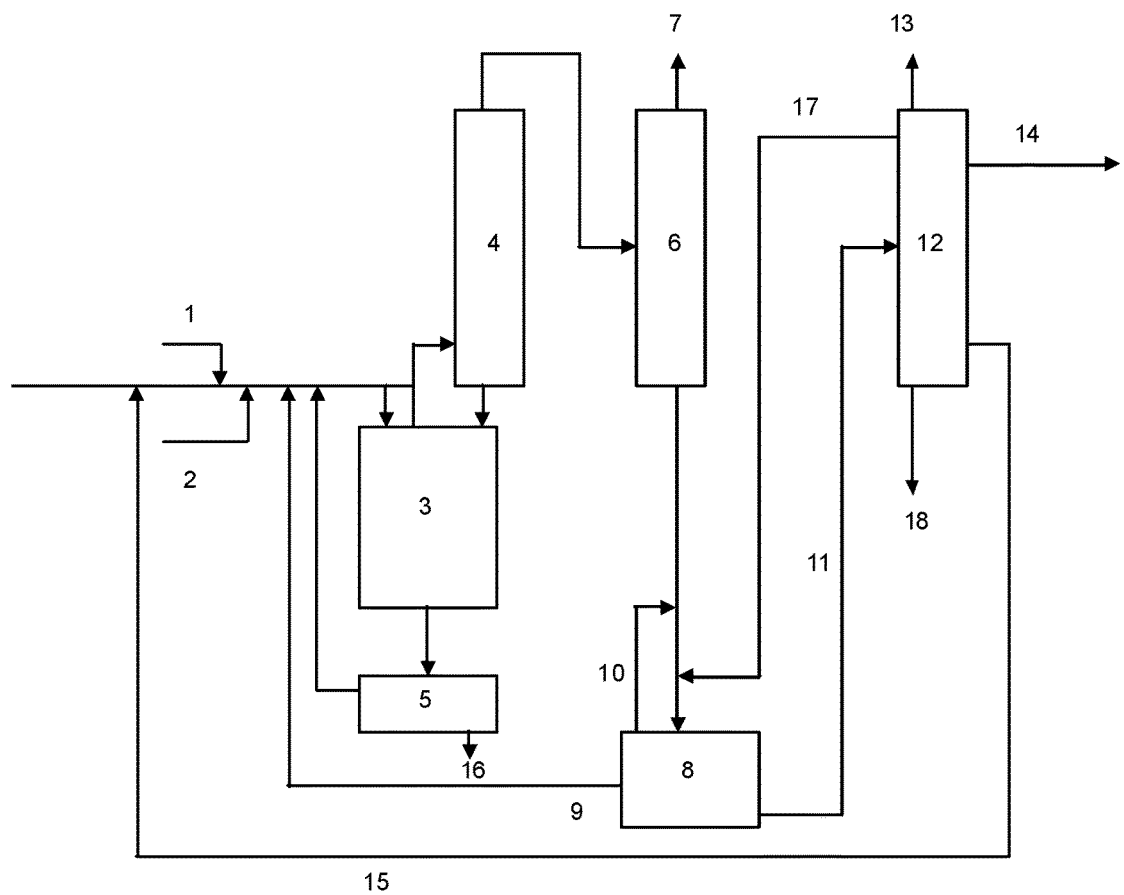

E-1-CHLORO-3,3,3-TRIFLUOROPROPENE PRODUCTION PROCESS FROM 1,1,3,3-TETRACHLOROPROPENE

CROSS REFERENCE TO RELATED APPLICATIONS

The present application is a continuation of U.S. application Ser. No. 14/153,500, filed on Jan. 13, 2014. The entire contents of each of U.S. application Ser. No. 14/153,500 are hereby incorporated herein by reference in their entirety.

TECHNICAL FIELD

The present disclosure involves a process for continuously producing E-1-chloro-3,3,3-trifluoropropene (E-1233zd). The process includes at least one 1,1,3,3-tetrachloropropene (1230za) liquid fluorination phase. This disclosure also includes an installation which is suitable for implementing this process on an industrial level.

TECHNICAL BACKGROUND

E-1-chloro-3,3,3-trifluoropropene (E-1233zd) can be produced by fluorinating 1,1,1,3,3-pentachloropropane (240fa). For example, documents U.S. Pat. Nos. 8,436,217 and 8,426,656 describe the liquid phase fluorination of 240fa to E-1233zd, with the presence of suitable catalysts such as $TiCl_4$ or a combination of $TiCl_4$ and $SbCl_5$.

FR 2768727 also explains that the fluorination of 240fa or 1230za can be completed with a catalyst such as $TiCl_4$.

US 2010/0191025 and U.S. Pat. No. 6,166,274 also describe the use of a catalyst for liquid phase fluorination of 1230za, with a view to obtaining E-1233zd: an ionic liquid based catalyst in the first document and a triflic or trifluoroacetic acid in the second document. US 2012/0059199 describes the liquid phase fluorination of 240fa without a catalyst. This document explains that a drawback to the non-catalyzed liquid phase process is the low reaction conversion rate. Several series reactors are therefore necessary to increase the overall conversion rate, each reactor contributes to improving the conversion rate.

US 2013/0211154 describes the use of increased reaction pressure as well as an agitated fluorination reactor to increase the rate of conversion in a non-catalyzed liquid phase 240fa process. Nevertheless, there is no indication of the conversion rate.

U.S. Pat. No. 6,987,206 describes the possibility of obtaining E-1233zd from 1230za as an intermediary, without indicating operational conditions.

An example of the non-catalyzed liquid phase fluorination reaction for 1230za is provided in U.S. Pat. No. 5,616,819. The pressure used is 200 psi (14 bar) and leads to the formation of oligomers, despite the shortness of the batch test.

U.S. Pat. No. 5,877,359 presents the non-catalyzed liquid phase fluorination of 1230za. The examples show that a very high molar ratio of 166 was used to obtain a full conversion on a short test batch. When the molar ratio falls to 12.6, a pressure of 600 psig (42 bar) is applied. On the other hand, the operational conditions of an extrapolable continuous process are not defined: molar ratio HF/1230za, reflux temperature, kind of by-products to be distilled. Nor are the productivity or stability over time of a process which is based on this reaction described.

There is still a need to develop a new continuous production process which can be extrapolated to E-1233zd without restrictive operational conditions (such as excessive pressure), high molar ratio or agitation in the fluorination reactor.

SUMMARY

Embodiments of this disclosure can help to overcome the difficulties of the known art. In particular, certain embodiments provide a new process for the production of E-1-chloro-3,3,3-trifluoropropene.

This may be achieved with the implementation of the fluorination of 1230za to E-1233zd using hydrogen fluoride in the liquid phase in the absence of a catalyst.

Embodiments of this disclosure also aim to provide an industrial process to produce E-1-chloro-3,3,3-trifluoropropene including the various separation and recycling operations.

Furthermore, embodiments of this disclosure aim to provide a facility that enables the implementation of various methods for carrying out the process.

BRIEF DESCRIPTION OF THE DRAWING

The disclosure will in the following be described in connection to preferred embodiments and in greater detail with reference to the appended exemplary drawing, wherein:

The FIGURE is a schematic representation of a mode of carrying out the procedure according to an embodiment of this disclosure and an installation for its implementation.

DETAILED DESCRIPTION

Embodiments of this disclosure are now described in more detail and without limitation in the description which follows.

According to embodiments of this disclosure, the process includes at least one stage during which 1,1,3,3-tetrachloropropene reacts with anhydrous hydrofluoric acid in the liquid phase in the absence of a catalyst with a HF/1,1,3,3-tetrachloropropene molar ratio between 3 and 20, at a temperature between 50° C. and 150° C. and an absolute pressure between 1 and 20 bar.

Embodiments of this disclosure also aim to provide a process for the production of E-1-chloro-3,3,3-trifluoropropene including (i) at least one stage during which 1,1,3,3-tetrachloropropene reacts with anhydrous hydrofluoric acid in the liquid phase in a reactor equipped with a drain and an effluent outlet; (ii) at least one stage for treating the effluent from the reactor in order to provide a flow A that includes the E-1-chloro-3,3,3-trifluoropropene, HCl, HF and Z-1-chloro-3,3,3-trifluoropropene and a flow B that mainly includes HF (e.g., at least 50% HF, preferably at least 70% HF in weight); (iii) at least one stage for recovering the hydrochloric acid from flow A, the hydrochloric acid being in flow C and flow D that includes E-1-chloro-3,3,3-trifluoropropene, HCl, HF and Z-1-chloro-3,3,3-trifluoropropene; (iv) at least one stage for purifying flow D from stage (iii) in order to purify the E-1233zd to a level preferably higher than or equal to 98%, more preferably higher than or equal to 99%, and particularly preferably higher than or equal to 99.9% in weight.

In addition, embodiments of this disclosure aim to provide a process for the production of E-1-chloro-3,3,3-trifluoropropene including (i) at least one stage in a reactor during which 1,1,3,3-tetrachloropropene reacts with anhydrous hydrofluoric acid in the liquid phase in the absence of a catalyst with a HF/1,1,3,3-tetrachloropropene molar ratio between 3 and 20, at a temperature between 50° C. and 150° C. and an absolute pressure between 1 and 20 bar, (ii) at least one stage for treating the effluent from the reactor in order to provide a flow A that includes the E-1-chloro-3,3,3-trifluoropropene, HCl, HF and Z-1-chloro-3,3,3-trifluoropropene and a flow B that mainly includes HF (e.g., at least 50% HF, preferably at least 70% HF in weight); (iii) at least one stage for recovering the hydrochloric acid from flow A, the hydrochloric acid being in flow C and flow D that includes E-1-chloro-3,3,3-trifluoropropene, HCl, HF and Z-1-chloro-3,3,3-trifluoropropene; (iv) at least one stage for purifying flow D from stage (iii) in order to purify the E-1233zd to a level preferably higher than or equal to 98%, more preferably higher than or equal to 99%, and particularly preferably higher than or equal to 99.9% in weight.

Preferably, before the purification stage, the flow from stage (iii) is subjected to at least one separation phase in order to provide a flow that mainly includes HF (e.g., at least 90% HF, preferably at least 98% HF, more preferably at least 99% HF in weight) that can be recycled in the reactor and a flow that includes the E-1-chloro-3,3,3-trifluoropropene, HCl, HF and the Z-1-chloro-3,3,3-trifluoropropene.

The separation stage is preferably by decantation, initiated at a temperature that may be between −50° C. and 50° C.

The treatment stage (ii) preferably involves a reflux column, preferably initiated at a temperature between 30° C. and 120° C. in order to provide the condensable flow B which is recycled in the reactor.

The recovery of HCl in stage (iii) is preferably obtained using a distillation column equipped with a reboiler at the bottom and a reflux system at the top. The temperature at the bottom may be between 20° C. and 110° C. The temperature at the top may be between −50 and 0° C.

The purification stage (iv) preferably includes at least one distillation stage, though at least two distillation stages are preferred.

Flow A may also include organic compounds, such as the intermediates of the fluorination reaction or co-products. Examples include, notably, dichlorodifluoropropene, trichloromonofluoropropene, fluorotetrachloropropane, pentafluoropropane, difluorotrichloropropane, dichlorotrifluoropropane and 1,3,3,3-tetrafluoropropene.

According to embodiments of this disclosure, the process may also include a drainage stage, wherein drainage collected in the reactor drain is, after treatment, recycled back to the reactor.

The HF/1,1,3,3-tetrachloropropne molar ratio is preferably between 5 and 15, more preferably between 9 and 12.

The reaction temperature is preferably between 80° C. and 120° C., more preferably between 90° C. and 110° C.

The fluorination reaction is preferably initiated at a pressure between 5 and 15 bar, more preferably between 7 and 12 bar. The fluorination reaction is preferably initiated in an unstirred reactor.

According to embodiments of this disclosure, the process may be implemented in continuous, discontinuous or batch mode. Continuous mode is preferable.

According to embodiments of this disclosure, the process may have the advantage of a surprisingly high yield and selectivity under mild conditions. Furthermore, these results may be obtained using a single reactor.

Unless stated otherwise, all of the percentages given below are percentages by weight.

Embodiments of this disclosure provide for the liquid phase fluorination of 1230za to E-1233zd by hydrogen fluoride, without a catalyzer.

With reference to the figure installation according to embodiments of this disclosure comprises a catalytic reactor 3 for the implementation of the reaction of fluorination of 1230za to E-1233zd.

The catalytic reactor 3 is supplied with an inlet line of 1,3,3,3-tetrachloropropene 2 and an inlet line of hydrogen fluoride 1. A means of heating is preferable for pre-heating the reagents before their arrival in the catalytic reactor 3.

The afore-mentioned inlet lines may feed the catalytic reactor 3 separately or may be connected together upstream of the catalytic reactor to supply it with a mix of reagents.

The catalytic reactor 3 is preferably a metal reactor. The metal of the reactor may be steel or stainless steel. However, other materials such as superaustenitic stainless steel or passive nickel-based alloys may be used. The absence of a catalyzer for the reaction is an advantage which avoids the corrosion phenomena known to experts in the field which occur when a fluorination catalyzer is used in this type of reactor.

All other installation equipment, notably the separation columns or distillation columns, may be made of metal.

The catalytic reactor 3 may include a heating jacket allowing the reaction mix to be brought to the desired temperature.

A drain line allows a quantity of undesirable products with high molecular weight which may form during the fluorination reaction to be purged. This flow also contains HF and recoverable organic compounds which are separated by a specific treatment 5 before being returned to the reactor. This treatment involves technologies known to experts in the field like decantation or azeotropic distillation, or preferably a combination of the two.

An outlet line for the products of the reaction is connected to the output of the catalytic reactor 3. This line transports a flow containing the desired product (E-1233zd), hydrogen chloride, hydrogen fluoride and co-products and by-products of the reaction.

The outlet line for products of the reaction supplies a preliminary separation unit 4, which is preferably a distillation column equipped with a reflux system at the top. This preliminary separation unit ensures a primary separation of HF from the rest of the products of the reaction.

At the top of the preliminary separation unit 4, a first intermediate line is connected, which is designed to collect the remaining products of the reaction, and supplies a separation unit 6 designed to separate hydrogen chloride, which is a co-product of the reaction.

Means of cooling may be used at the first intermediate line so that the first separation unit can operate at the desired temperature.

The separation unit 6 is preferably a distillation column equipped with a reboiler at the bottom and a reflux system at the top. It may for example be operated at a pressure slightly lower than that of the catalytic reactor 3. At the top of the separation unit, an outlet line for hydrogen chloride is connected, through which a flow 7 containing mainly hydrogen chloride is removed. Traces of E-1233zd or light co-products such as 245fa or E-1234ze may be present in this flow.

The HCl product is preferably removed as HCl solution after adiabatic or isothermal absorption in water. The HCl may be purified by passing the gas through alumina towers to achieve desired quality.

At the bottom of the separation unit 6, a separation system 8 is connected to allow the separation of HF and other organic products. This separation system comprises a first phase separation unit. The phase rich in HF may thereby be brought to a separation unit which is preferably an azeotropic separation unit where the fraction at the bottom of the column is enriched in HF before being recycled in the reactor 3 through the line 9 (99.7% HF, 0.3% E-1233zd) The azeotropic fraction 10 collected at the top is recycled towards the separation unit 8.

The phase rich in organic compounds will be collected by line 11 (approx. 90-95% E-1233zd, 3-5% HF, 1-5% Z-1233zd and 0.1-2% co-products and intermediate products) and may be treated by a downstream purification unit 12 comprising at least one additional azeotropic distillation column allowing final separation of HF and a final purification unit allowing E-1233zd to be obtained with a purity higher than or equal to 98% (flow 14 in the figure. In embodiments, there may be two azeotropic distillation columns in the process; an azeotropic column integrated into separation system 8 after a decanter, and an azeotropic column in purification unit 12.

The purification unit 12 comprises preferably a first distillation column to remove lights products (like 245fa, E-1234ze or remaining HCl for example) that are collected out of the process through outlet line 13.

The resulting flow of the first distillation column is then treated by an azeotropic distillation column to finalize the separation of HF. Azeotropic composition is thus collected by line 17 and recycled towards the separation unit 8. The composition of this flow is similar to that of the composition of line 10, that is, mainly the azeotropic mixture of HF and E-1233zd.

The resulting flow of the azeotropic distillation column is finally treated with at least one purification column, preferably two columns, to remove a fraction containing mainly the cis-isomer and intermediates (like 1232, 1231 isomers) recycled back to the reactor through line 15 and non valuable heavies compounds eliminated by outlet line 18.

E-1233zd is collected through line 14 with a purity greater than or equal to 98%, more preferably higher than or equal to 99%, and particularly preferably higher than or equal to 99.9% in weight.

EXAMPLES

The following examples illustrate embodiments of the disclosure without limiting the disclosure.

A first stage consists of preparing the raw material. The 1,1,3,3-tetrachloropropene is obtained through the dehydrochlorination of 1,1,1,3,3-pentachloropropane in the presence of anhydrous ferric chloride.

Example 1

Preparation of 1230za by Dehydrochlorination of 240fa

In a glass reactor equipped with a double jacket and a reflux, we introduce 1441.6 g of 1,1,1,3,3-pentachloropropane, with a purity of 99.6%. The top of the reactor is flushed with a nitrogen flow rate of 4 l/h to form an inert atmosphere. We then introduce 14.4 g of anhydrous ferric chloride before activating the agitation at 800 rpm. The reflux is supplied with a fluid kept at 20° C. The gas outlet of the condenser is connected to a water bubbler for trapping the HCl which is given off during the dehydrochlorination reaction. The mix is then heated to between 75° C. and 80° C. for several hours (approx. 4 hours) until no more gas is given off. 1195.6 g of remaining solution is drained from the flask. The mix obtained is filtered to eliminate the ferric chloride in suspension, then analyzed by gas chromatography.

TABLE 1 dehydrochlorination of 240fa: composition of mix

| Compound (mol %) | Before reaction | After reaction |
|---|---|---|
| 1230za | 0.055 | 92.613 |
| 250fa | 0.035 | 0.025 |
| 240fa | 99.58 | 6.062 |
| $C_2Cl_6$ | 0.051 | 0.052 |
| 240db | 0.157 | 0.159 |

Example 2

Distillation of 1230za

The 1230za of weak purity then undergoes classic laboratory distillation involving a column with 10 plates, a coolant, a vacuum pump, a flask and receiving flasks. The distillation is carried out under a vacuum of 25 mbar, giving the 1230za a boiling point of 53° C. We obtain a raw material of good purity, with the following composition: 99.33% of 1230za, 0.02% 250fa, 0.15% 240fa, 0.009% $C_2Cl_6$ and 0.001% 240db.

Example 3

Continuous Liquid Phase Fluorination of 1230za

The equipment used comprises an autoclave with a capacity of 1 liter with a double jacket, made of stainless steel grade 316L. Means of measuring temperature and pressure are required. The openings at the top of the autoclave allow the reagents to be introduced and the products to be removed. A condenser is provided at the top, as well as a valve for regulating pressure. The temperature of the condenser is checked with an independent thermostatically controlled water bath. Its function is to return part of the non-reacted HF and the intermediates to the reactor.

The products of the reaction are continuously extracted during the reaction. The outlet gas flow passes into a washing unit which collects the hydracids HF and HCl, and is then cooled in the liquid nitrogen. The molar distribution of the outlet gas products is analyzed periodically by GPC (gas phase chromatography).

At the end of the test, the reaction medium is depressurized and slowly heated in order to remove the residual HF. During this degasification period, the organic compounds which may have been formed are also recovered, after passing through the washing unit in order to remove HF and HCl from the gaseous flow. In the final stage, the autoclave is opened and emptied.

The raw material prepared in example 2 is used for a fluorination reaction.

A quantity of 300 g of HF is introduced into the autoclave. The temperature of the reactor is adjusted to 92-93° C. in the liquid phase. Pressure regulation is carried out at 10 bar abs. The reactants are then introduced at the following rates: 20 g/h of 1230za and 20 g/h of HF. The molar ratio of HF to the organic compound is therefore 9. The establishing of an acceptable mass balance between input and output is checked regularly. The composition of the output stream is followed by GPC analysis and recorded in table 2:

TABLE 2 molar composition of output gas (1230za input flow of 20 g/h)

| Time | Molar composition of output | | | |
|---|---|---|---|---|
| | F1233zd-E | F1233zd-Z | F1234ze(E + Z) | F245fa |
| 5.5 h | 90.6% | 3.9% | 1.4% | 2.2% |
| 23 h | 92.1% | 3.7% | 1.5% | 1.4% |
| 29.2 h | 91.6% | 3.7% | 1.6% | 1.4% |
| 46.7 h | 92.4% | 3.7% | 1.5% | 1.1% |
| 53.7 h | 92.1% | 3.6% | 1.6% | 1.2% |

The rest of the composition is made up of intermediate products (1231, 1232, 241, 242, 243) and/or unidentified products.

The F1233zd-E productivity of the reactional system is 0.31 mol/h/L.

Example 4

Continuous Fluorination in the Liquid Phase of 1230za

The procedure outlined in example 3 is reproduced, but with double the feed rates for organic matter and HF, thus 40 g/h of 1230za and 40 g/h of HF. The molar ratio of HF to the organic compound remains unchanged at 9.

The composition of the output stream is followed by GPC analysis and detailed in table 3:

TABLE 3 molar composition of output gas (1230za input flow of 40 g/h)

| Time | Molar composition of output | | | |
|---|---|---|---|---|
| | F1233zd-E | F1233zd-Z | F1234ze(E + Z) | F245fa |
| 5.5 h | 92.5% | 3.8% | 1.0% | 1.0% |
| 23.1 h | 93.7% | 3.7% | 0.6% | 0.7% |
| 29.1 h | 93.5% | 3.8% | 0.5% | 0.6% |
| 46.6 h | 91.4% | 4.5% | 0.2% | 0.1% |

The productivity of the F1233zd reactional system is 0.68 mol/h/L.

Following the tests described in examples 3 and 4, the reactor was emptied. The hydracids were trapped in water, the light organic substances were caught in a cold trap and the remaining organic substances in the reactor bottom were recovered. The liquid level in the reactor fell during the test and the composition of elements in the reactor is as follows: 11.3 g of HF, 5.6 g of HCl, 9 g of light organic substances and 127 g of organic compounds accumulated in the reactor. The chromatographic analysis of these two fractions was carried out and enabled the overall composition of the liquid mixture to be prepared as a mass percentage: 7.4% HF, 3.7% HCl, 3.5% E-1233zd, 0.25% Z-1233zd, 18.2% of 1230za, 2.4% of 1231, 14.8% of 1232, 49.2% of unidentified compounds. This means that 2.3% of tars were formed.

The conversion of the whole test is calculated on the basis of 27.9 g of 1230za recovered in the liquid phase compared with 3059 g added to the total, thus 99.1%. E-1233zd selectivity over the whole continuous test (example 3 and example 4) is 89.2%, Z-1233zd selectivity is 3.8%, 2% in 1232, 0.7% in 1234zeE, 0.7% in 245fa and 2.9% in unknown products.

Example 5

Continuous Fluorination in the Liquid Phase of 1230za

The procedure outlined in example 3 is reproduced. A quantity of 300 g of HF is introduced into the autoclave. The temperature of the reactor is adjusted to 91-92° C. in the liquid phase. Pressure regulation is carried out at 10 bar abs. The molar ratio of HF to the organic substances is adjusted at 10 and a longer run has been carried out to establish the stability of the continuous process during 200 h. 40 g/h of 1230za and 44 g/h of HF are fed continuously to the reactor. The establishing of an acceptable mass balance between input and output is checked regularly.

The composition of the output stream is followed by GPC analysis and detailed in table 4:

TABLE 4 molar composition of output gas (molar ratio of 10, longer run)

| Time | Molar composition of output | | | |
|---|---|---|---|---|
| | F1233zd-E | F1233zd-Z | F1234ze(E + Z) | F245fa |
| 5 h | 92.7% | 3.9% | 0.75% | 1.9% |
| 10 h | 93.7% | 2.7% | 1.5% | 1.7% |
| 16.5 h | 92.6% | 3.8% | 1.0% | 1.4% |
| 33 h | 92.5% | 3.8% | 1.2% | 1.1% |
| 38.5 h | 92.8% | 3.7% | 1.1% | 1.1% |
| 44.5 h | 92.6% | 3.9% | 1.1% | 1.2% |
| 62 h | 92.8% | 3.6% | 1.2% | 0.9% |
| 68 h | 92.5% | 3.7% | 1.2% | 0.9% |
| 86 h | 92.9% | 3.6% | 1.1% | 0.8% |
| 92 h | 92.8% | 3.6% | 1.1% | 0.9% |
| 114 h | 92.7% | 3.7% | 1.0% | 0.8% |
| 120 h | 93.0% | 3.6% | 1.1% | 1.0% |
| 137 h | 93.4% | 3.6% | 1.1% | 0.6% |
| 143 h | 92.8% | 3.6% | 1.2% | 0.7% |
| 161 h | 93.4% | 3.5% | 1.5% | 0.6% |
| 167 h | 92.9% | 3.6% | 1.2% | 0.7% |
| 185 h | 93.1% | 3.7% | 1.0% | 0.6% |
| 191 h | 93.1% | 3.6% | 1.0% | 0.7% |
| 193 h | 93.2% | 3.7% | 0.9% | 0.7% |
| 200 h | 93.3% | 3.7% | 0.9% | 0.7% |

The rest of the composition is made up of intermediate products (1231, 1232, 241, 242, 243) and/or unidentified products.

Following the tests described in example 5, the reactor was emptied. The hydracids were trapped in water, the light organic substances were caught in a cold trap and the remaining organic substances in the reactor bottom were recovered.

No 1230za was detected. Conversion is thus 100%. Selectivity towards E-1233zd is 90-92%. The E-1233zd productivity is 0.68 mol/h/l.

150 g of remaining organic substances were recovered in the reactor bottom.

Considering that 8 kg of 1230za were fed along the run, this means that only 1.8% of tars were formed.

While illustrative embodiments of the invention have been described herein, the present invention is not limited to the various preferred embodiments described herein but includes any and all embodiments having equivalent elements, modifications, omissions, combinations (e.g. of aspects across various embodiments), adaptations and/or alterations as would be appreciated by those in the art based on the present disclosure. The limitations in the claims are to be interpreted broadly based on the language employed in the claims and not limited to the examples described in the present specification or during prosecution of the application, which examples are to be construed as non-exclusive.

The invention claimed is:

1. A production process for the production of E-1-chloro-3,3,3-trifluoropropene, the process comprising:
   (i) at least one stage during which 1,1,3,3-tetrachloropropene reacts with anhydrous hydrofluoric acid in the liquid phase in a reactor equipped with a drain and an effluent outlet; wherein HF and recoverable organic compounds are collected in the reactor drain, treated by at least one of decantation and azeotropic distillation, and recycled back to the same reactor;
   (ii) at least one stage for treating the effluent from the reactor in order to provide a flow A that comprises E-1-chloro-3,3,3-trifluoropropene, HCl, HF and Z-1-chloro-3,3,3-trifluoropropene and a flow B that comprises at least 50% HF in weight;
   (iii) at least one stage for recovering the hydrochloric acid from flow A, the hydrochloric acid being in flow C and flow D that includes E-1-chloro-3,3,3-trifluoropropene, HCl, HF and Z-1-chloro-3,3,3-trifluoropropene;
   (iv) at least one stage for purifying flow D from stage (iii) in order to purify the E-1233zd to a level higher than or equal to 98% in weight.

2. The production process of claim 1, wherein before the purification stage (iv), the flow D from stage (iii) is subjected to at least one separation phase in order to provide a flow E that comprises at least 50% HF in weight that can be recycled to the reactor and a flow F that comprises E-1-chloro-3,3,3-trifluoropropene, HCl, HF and Z-1-chloro-3,3,3-trifluoropropene.

3. The production process of claim 2, wherein the separation stage is by decantation, initiated at a temperature between −50° C. and 50° C.

4. The production process of claim 1, wherein the treatment stage (ii) involves a reflux column, initiated at a temperature between 30° C. and 120° C. in order to provide the flow B which is recycled to the reactor.

5. The production process of claim 1, wherein the recovery of HCl in stage (iii) is obtained using a distillation column equipped with a reboiler at the bottom and a reflux system at the top.

6. The production process of claim 5, wherein the temperature at the bottom is between 20° C. and 110° C. and the temperature at the top is between −50 and 0° C.

7. The production process of claim 1, wherein the purification stage (iv) comprises at least one distillation stage.

8. The production process of claim 1, wherein, in the reactor, the HF/1,1,3,3-tetrachloropropene molar ratio is between 5 and 15.

9. The production process of claim 1, wherein reaction temperature is between 80° C. and 120° C.

10. The production process of claim 1, wherein the fluorination reaction is initiated at a pressure between 5 and 15 bar.

11. The production process of claim 1, wherein the fluorination reaction is initiated in an unstirred reactor.

12. The production process of claim 1, wherein 1,1,3,3-tetrachloropropene reacts with anhydrous hydrofluoric acid in the liquid phase in a single reactor equipped with a drain and an effluent outlet.

* * * * *